United States Patent
Beyar et al.

(10) Patent No.: US 11,389,220 B2
(45) Date of Patent: Jul. 19, 2022

(54) CORE AND SHELL COUPLING OF A COMPOSITE MATERIAL BONE IMPLANT

(71) Applicant: Carbofix In Orthopedics LLC, Wilmington, DE (US)

(72) Inventors: Mordechay Beyar, Tel-Aviv (IL); Oren Globerman, Kfar-Shemaryahu (IL)

(73) Assignee: CarboFix Spine Inc., Ocean Isle Beach, NC (US)

( * ) Notice: Subject to any disclaimer, the term of this patent is extended or adjusted under 35 U.S.C. 154(b) by 330 days.

(21) Appl. No.: 16/601,615

(22) Filed: Oct. 15, 2019

(65) Prior Publication Data

US 2020/0038082 A1 Feb. 6, 2020

Related U.S. Application Data

(63) Continuation of application No. 14/960,563, filed on Dec. 7, 2015, now Pat. No. 10,448,983.

(51) Int. Cl.
*A61B 17/04* (2006.01)
*A61B 17/86* (2006.01)
*A61F 2/08* (2006.01)
*A61B 17/00* (2006.01)

(52) U.S. Cl.
CPC .......... *A61B 17/866* (2013.01); *A61B 17/864* (2013.01); *A61B 2017/00526* (2013.01); *A61B 2017/00964* (2013.01); *A61B 2017/8655* (2013.01)

(58) Field of Classification Search
CPC combination set(s) only.
See application file for complete search history.

(56) References Cited

U.S. PATENT DOCUMENTS

| | | | |
|---|---|---|---|
| 6,921,402 B2 | 7/2005 | Contiliano et al. | |
| 2009/0163955 A1 | 6/2009 | Moumene et al. | |
| 2013/0211465 A1 | 8/2013 | Savage | |
| 2015/0297267 A1* | 10/2015 | Gepstein | A61L 31/126 606/264 |
| 2017/0156773 A1 | 6/2017 | Beyar et al. | |

FOREIGN PATENT DOCUMENTS

| | | |
|---|---|---|
| EP | 0799124 | 10/1997 |
| WO | WO 2010/069496 | 6/2010 |
| WO | WO 2014/138736 | 9/2014 |

OTHER PUBLICATIONS

Restriction Official Action dated Sep. 4, 2018 From the US Patent and Trademark Office Re. U.S. Appl. No. 14/960,563. (7 pages).
Second Restriction Official Action dated Dec. 26, 2018 From the US Patent and Trademark Office Re. U.S. Appl. No. 14/960,563. (7 pages).

* cited by examiner

*Primary Examiner* — Sameh R Boles

(57) ABSTRACT

Fiber-reinforced polymer matrix composite material bone screws having threads surfaced with a metallic layer are described. In some embodiments, the metallic layer comprises a plurality of anchors placed to engage with the composite material and resist shearing when the bone screw is inserted or removed.

25 Claims, 5 Drawing Sheets

CORE AND SHELL COUPLING OF A COMPOSITE MATERIAL BONE IMPLANT

RELATED APPLICATIONS

This application is a continuation of U.S. patent application Ser. No. 14/960,563, filed on Dec. 7, 2015. The contents of the above applications are all incorporated by reference as if fully set forth herein in their entirety.

FIELD AND BACKGROUND OF THE INVENTION

The present invention, in some embodiments thereof, relates to composite material bone implant devices—mainly, but not limited to, screw constructs for such devices; and more particularly, but not exclusively, to such devices as applied to implant devices constructed of fiber-reinforced polymer matrices.

Bone implant screws (bone screws) are used to secure and stabilize bone implants, for example, by attachment through an aperture of a bone implant into bone, and/or by attaching other bone implant parts to each other.

Normally, bone screws are made of metal, for example, titanium and/or stainless steel. Although metallic implants provide numerous advantages, the metals potentially obstruct visualization of the implant and surrounding tissue upon using fluoroscopy, CT and/or MR imaging. Such imaging means are important for follow-up evaluation, including for identification of exact screw location, and/or status of tissue (for example, bone, nerve tissue, and/or potentially cancerous tissue) surrounding the bone implant and/or bone screw. Furthermore, metallic implants interfere with radiotherapy given to oncology patients. The relatively large electronic mass and associated scattering phenomena reduce radiation effectiveness and necessitate radiation in higher doses that can further provoke side-effects on surrounding tissue.

Metal construction normally provides adequate bending and torsion strength to resist implant fracture. However, the rigid metal implant, having different elasticity than that of the bone, may contribute to stress shielding; leading, for example, to bone loss. Metals such as stainless steel may cause biocompatibility problems related to corrosion and sensitization reactions (mainly due to allergy to nickel). Resistance of metals to fatigue loads is potentially poorer than a resistance of some composite materials to a similar fatigue load.

Non-metal, composite material, implants are currently available on the market; for example, cage and vertebral body replacement devices made of carbon-polyether ether ketone (PEEK). Lumbar and/or cervical cages are also produced from PEEK, carbon fiber reinforced polymer or carbon. Carbon fiber-reinforced PEEK is also used for other bone applications, such as intramedullary nails and bone plates (CarboFix Orthopedics Ltd.).

SUMMARY OF THE INVENTION

There is provided, in accordance with some exemplary embodiments, a bone screw having screw threads for rotating insertion to a bone, the bone screw comprising: a body formed from composite material comprising a fiber-reinforced polymer matrix; and a metallic layer surfacing the body with at least one metallic ply covering at least a region of the screw threads; wherein a plurality of anchor structures having a thickness dimension at least 50% of the thickness of the metallic ply are formed out of the material of the at least one metallic ply to engage with the composite material and resist a shearing force applied to the metallic layer and directed along the screw threads when the screw is rotated within the bone.

According to some embodiments, the metallic layer comprises at least one from among the group comprising titanium and a titanium alloy.

According to some embodiments, the titanium or titanium alloy is anodized.

According to some embodiments, a plurality of the anchor structures are formed in the at least one metallic ply as openings filled with the composite material.

According to some embodiments, the openings are formed as convolutions of an edge of the at least one metallic ply.

According to some embodiments, the openings are formed as apertures in the at least one metallic ply.

According to some embodiments, a plurality of the anchor structures are formed by indentation of an outer surface off the at least one metallic ply.

According to some embodiments, the indented anchor is within a recessed region between two turns of the screw thread.

According to some embodiments, the indented anchor protrudes by at least 50% of the thickness of the at least one metallic ply into the composite material, relative to the non-indented surrounding inner surface of the metallic ply.

According to some embodiments, the anchor structures are formed in a repeating pattern along the metallic ply.

According to some embodiments, the screw is cannulated.

According to some embodiments, the at least one ply comprises a strip wound around the body.

According to some embodiments, a first portion of the strip overlies and is welded to a second portion of the strip.

According to some embodiments, a free edge of the first portion of the strip lies in a recess between two turns of the screw thread.

According to some embodiments, the at least one ply comprises a tube compressed onto the body.

According to some embodiments, the tube is welded to another ply of the metallic layer.

There is provided, in accordance with some exemplary embodiments, a method of securing a metallic outer layer to a composite material construction bone screw body, the method comprising: preparing a ply for forming the metallic outer layer with a plurality of anchoring structures; and attaching the ply onto the bone screw body, such that the plurality of anchoring structures interpenetrates with composite material of the bone screw body underneath recesses defined between adjacent thread windings of the bone screw.

According to some embodiments, the attaching comprises winding the ply around the bone screw body.

There is provided, in accordance with some exemplary embodiments, a bone screw having screw threads for rotating insertion to a bone, the bone screw comprising: a body formed from composite material comprising a fiber-reinforced polymer matrix; and a metallic layer surfacing the body with at least one metallic ply covering at least a region of the screw threads; wherein a plurality of anchor structures are attached to the inner surface of the metallic ply, each anchor structure comprising a thickening by at least 50% of the thickness of the metallic ply, to engage with the composite material for anchoring the metallic ply thereto.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
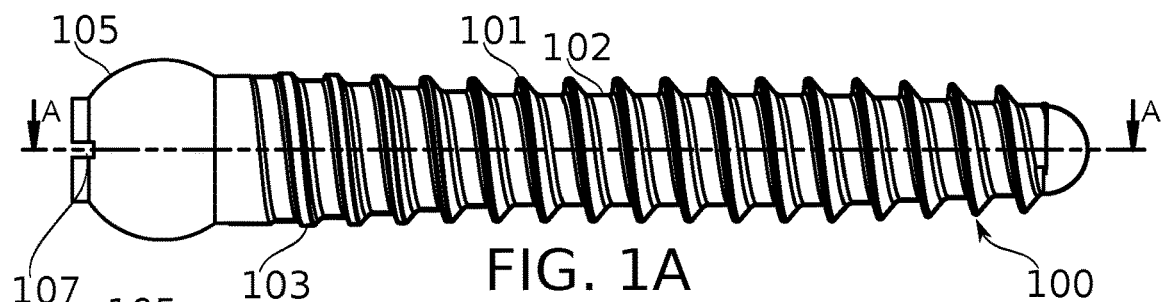
FIGS. 1A-1B schematically illustrate in profile (FIG. 1A) and in cross-section (FIG. 1B) a composite construction bone screw having a metallic outer layer, according to some exemplary embodiments of the invention.

The present invention, in some embodiments thereof, relates to composite material bone implant devices—mainly, but not limited to, screw constructs for such devices; and more particularly, but not exclusively, to such devices as applied to implant devices constructed of fiber-reinforced polymer matrices.

Overview

A broad aspect of some embodiments of the current invention relates to attachment of a metallic outer layer to a bone screw having a body of composite construction, the attachment being suitable to resist shear forces (for example, from a bone plate and/or a bone) tending to detach the metallic outer layer from the body upon screw insertion and/or removal. In some embodiments, the bone screw is for use with a spinal bone implant system. Optionally, such a bone screw is named and/or characterized as a spine screw, a pedicle screw, a screw that enters a vertebra, a screw that connects a plate and/or rod to a vertebra, and/or a screw that connects a spine cage to vertebrae. A typical pedicle screw, for example, screws into and anchors within bone (a pedicle of a vertebra), while having a head connectable to additional hardware, which may bridge between adjacent pedicle screw heads.

Optionally, the head swivels to accommodate movement. For anchoring in bone, pedicle screw threads are optionally coarse-threaded (for example, a pitch of about 2 mm or more per turn). In some embodiments, the bone screw is for use in another bone implant role; for example, used in securing a bone plate or bone nail.

In some embodiments, at least a threaded portion of a bone screw shaft comprises a layer (optionally, metallic) providing an outer surface of the bone screw. The layer coats and/or is formed against an inner screw body. Optionally, the body is of composite fiber-reinforced construction; for example, carbon fiber-reinforced polyether ether ketone (CFR-PEEK), or another medical grade fiber-reinforced composite material. Optionally, the screw body is cannulated.

Use of a composite fiber constructed body potentially provides advantages (compared to an equivalent all-metal body) such as, for example, reduced stress shielding and lower imaging artifact incidence, optionally with strength that is about as high or higher than an all-metal equivalent. Combined with a composite fiber-reinforced matrix screw body, a metal outer surface provides a potential advantage for toughening the surface against wear. For example, the metallic layer protects threads against cracking and/or shedding of particles during insertion, removal, and/or operation during implantation.

In some embodiments, the metallic outer surface layer comprises titanium, for example, pure titanium (Ti) and/or a titanium alloy such as Ti-6Al-4V, and/or another metal. The metal is optionally shaped, for example, as a foil, coating, tube, and/or shell. Optionally, the metal is anodized. In some embodiments, the thickness of the metallic outer surface layer is, for example, between 1 μm and 200 μm. Optionally, the thickness is, for example, between 4-5 μm, 10-50 μm, 2-9 μm, 70-90 μm, 20-60 μm, 50-100 μm, or within another range of thicknesses having the same, greater, lesser, and/or intermediate bounds. Optionally, the thickness is chosen to be thin enough to significantly prevent artifacts in imaging; for example, to prevent at least 50%, 70%, 90%, 95%, intermediate, or greater percentages as compared to artifacts generated (for example, in MRI or CT imaging) if the whole screw were formed of titanium alloy. Artifact magnitude is optionally expressed as a size (for example, as an area, volume, and/or distance affected by the artifact within an image or image set). Additionally or alternatively, the artifact is expressed as an intensity; for example, in terms of absolute or relative changes in pixel value, and/or apparent radiopacity in a region. With respect to imaging artifact reduction, it is also noted that titanium, compared to many metals used in biocompatible applications, provides a potential advantage in terms of its high strength/toughness in relation to its linear attenuation coefficient (an index of radiopacity).

In part, the metallic layer itself is optionally a protection against shear forces (for example, by providing a tougher surface than provided by fiber-reinforced composite polymer material). Potentially, however, adhesive contact between a composite material such as CFR-PEEK and a metal such as titanium is not inherently strong. In some embodiments, the region of contact and/or adherence between the metallic layer and the underlying body is exposed to shear forces experienced during insertion and/or removal of the bone screw. Potentially, shear induces peeling, tearing, and or lifting of a surface layer. Moreover, while it is a potential advantage for a metallic outer surface layer to be sufficiently thin to reduce imaging artifacts due to the relatively high radiopacity of metals, a thinner layer is potentially also more vulnerable to shearing damage (for example, tearing) by forces experienced during insertion and/or removal.

In some embodiments, shear resistance is increased by providing the outer layer and/or the underlying body with structures that interpenetrate with material of the body and the layer. The screw threads themselves (though they may represent a kind of interpenetration along the longitudinal dimension) potentially do not geometrical interlock in the right orientation to resist shearing during rotational insertion. In particular, thread height is typically constant following along the thread pitch; the thread is shaped to guide, rather than cut across, the shear vectors associated with screw insertion and removal. Potentially more effective shear-resisting geometrical interlocking provides a component which sharply interrupts and/or lies across the directions of shear, rather than runs alongside them. In some embodiments, anchoring moreover comprises structures that need to move in more than one direction in order to come free, or are embedded (for example, by a loop) so that they cannot be freed without breakage of their supporting surroundings as well.

An aspect of some embodiments of the invention relates to shaping the material of one or more metallic plies of an outer layer with a plurality of anchoring structures that interpenetrate with material of the composite material body underneath. In some embodiments, a dimension of the anchoring structure is at least 25%, 50%, 75%, 100%, or more of the thickness of the metallic ply itself. The dimension (or the whole anchor) is optionally formed by removal and/or deformation of the ply material. In some embodiments, recesses are provided to a foil edge or surface which becomes filled with material from the screw body during manufacture, interlocking the two. Optionally, protrusions of the foil edge push away and/or into material of the screw body, interlocking the two. In some embodiments, the improvement of shear resistance as a result of such geometrical interlocking is by a factor of about 2, 3, 4, 5, 8, 10, or another greater, smaller, or intermediate value. In an example, the inventors have found that a test screw of outer diameter 6.5 mm and without geometrical interlocking withstands about 2.5 N·m of torque before separation of a titanium outer layer (thickness in the range of about 100-150 μm) from a composite material screw body occurs. Torque is applied, for example, during screw insertion and screw removal, as the movement of the screw is resisted by the bone or other material in which it is embedded. With geometrical locking (for example as described in relation to FIGS. 1C-1D), the torque of separation was about 6 N·m. Optionally, another size, shape, and/or topology of geometrical locking (for example, the addition of loop structures such as described in relation to FIG. 1E) is used, potentially increasing resistance to separation under torque.

For example, edges of a metal foil are shaped with convolutions forming protrusions and recesses. In some embodiments, the edge shape comprises a repeating pattern; for example, combed, crenellated, toothed, dovetailed, undulated, wave, fluted, scalloped, and/or another other regular or irregular pattern. In some embodiments, the edge shape is non-repeating. In some embodiments, a portion of the outer layer material is perforated (for example, a portion near but not breaking an edge), creating a plurality of holes through the material. A shaped edge optionally comprises an edge of a metallic shell or winding which deviates from a straight line when unwrapped (and/or, a curve which is non-deviating relative to a circumference when wrapped) by, for example, about 0.1-3 mm; for example, about 0.5 mm, 1 mm, 1.5 mm, 2 mm, 3 mm, or another larger, smaller, or intermediate deviation. Where the foil is perforated along an edge (optionally without changing the edge itself), the closest distance of the perforation to the edge ranges, for example, up to about 0.1-2 mm, or another larger, smaller, or intermediate distance. In some embodiments, perforations are provided further from the edge of the metal foil. In some embodiments, a metal outer layer is provided by another coating method (for example, sputter coating), and perforated, for example, by masking before coating, by cutting and/or ablation of material after coating, and/or by another method.

In some embodiments (optionally additionally), the outer layer material is formed with protrusions (optionally in a repeating pattern, for example, a pattern of spacings following an edge of a ply of the outer layer material) that extend into the material of the screw body, and/or with recesses that allow the material of the body to break a plane or tangent plane of an inner surface of the outer layer material.

Optionally, protrusions are formed on one surface by pressure from the opposite surface (for example, dimpling the outer surface of a metal ply to produce a protrusion on its inner surface). Optionally, protrusions are formed by folding at an edge, for example, folding a whole or a portion of an edge region (at any angle up to doubled-over) so that it protrudes into the material of the body.

Additionally or alternatively, in some embodiments, spaced protrusions (in the form, for example, of grains, wires, blocks, billets, disks, and/or another shape) are welded and/or adhered to the inner surface. The protrusions are optionally spaced in a repeating pattern. Optionally, the protrusions themselves comprise at least partially lateral protrusions to enhance anchoring. In some embodiments, anchor structures comprise features which protrude from or remove at least 50%, 75%, 100%, or another greater, lesser or intermediate amount of the average thickness of the metal foil away from the anchors. For example, in the case of 100% change, protrusions double the thickness of the foil, or cutaways completely remove the foil in their area.

Additionally or alternatively, the inner surface is grooved and/or pitted. In some embodiments, the outer surface of a metal foil (before application to the body, and/or after application to the body wherein the metal foil comprises two applied plies) remains smooth and/or undisrupted while an inner surface is shaped with anchoring structures.

In some embodiments, the outer layer material is embossed (for example, by stamping) to intrude partially into material of the screw body, and/or vice versa to allow such intrusion by the screw body. In some embodiments, the outer layer material is feathered (thinned toward the edges), to allow body material to lap over it. It is to be understood that anchors of different types are optionally provided in the same screw and in any combination.

In some embodiments, the inner surface is provided with anchor loops, for example, by welding a metallic mesh and/or curving wire at intervals along a surface of the outer layer material (an inner surface, and/or an outer surface, beyond which the welded material protrudes to reach the material of the screw body). This provides a potential advantage by creating interlacing of outer layer and inner body material that cannot be broken without physically breaking apart one of the two interpenetrating materials.

In some embodiments where the through-integrity of a portion of the outer layer material is broken by a perforation, lateral protrusion, and/or edge shaping, full and/or faired (smoothed-out) metal coating at that portion is nonetheless maintained by overlaying the broken-through portion with outer layer material (for example, foil). In some embodiments, a single winding overlies itself at each winding (smooth edge over rough for example). Additionally or alternatively, a plurality of windings is provided, with a lower winding ply providing anchoring for an outer ply that optionally completes and/or fairs it. Optionally, overlapping plies are welded and/or otherwise adhered together to make an at least two-ply outer layer. Additionally or alternatively, an outer ply is coated onto the inner ply and/or the composite material of the screw body by another means (for example, sputter coating, electroplating, or another method where a sheet of metal forms on the device itself), with the anchored ply serving as a shear-resistant base.

In some embodiments, a polymer/metal join by geometrical interpenetration is used as a basis for the attachment of further metal layers based on metal-metal attachment methods such as welding (laser welding, for example) and/or crimping.

Optionally, welding is before or after operations to compress a metallic layer onto the screw body.

In some embodiments, protrusions and/or cutaways are provided on the thread body itself (that is, on the region of the thread protruding from the valley between thread windings). Protrusions and/or cutaways on either or both sides (distal/proximal) of the winding are optionally provided. In some embodiments, protrusions and/or cutaways are provided between windings of the thread body (in the valleys between thread windings). Optionally, any combination of these positions is provided.

An aspect of some embodiments of the invention relates to adding radiopacity to a substantially radiolucent metallic outer layer by attachment of radiopaque markers to it.

In some embodiments, the radiopacity of metal material attached to an outer coating layer is selected to be large enough, everywhere, or in one or more selected areas, to serve as a position marker. For example, an attached anchor is selected to be relatively large, and/or to comprise a relatively radiopaque material such as gold, platinum, rhenium, tungsten, tantalum, or another radiopaque material. In some embodiments, a radiopaque marker is more radiopaque than a substantially radiolucent outer coating layer (for example, radiopaque to X-rays at one or more selected imaging energies) by a factor of at least 5, 10, 20, 25, or another larger, smaller, or intermediate factor. In some embodiments, a substantially radiolucent outer layer blocks less than 50%, less than 25%, less than 10%, less than 5%, or less that another greater, smaller, or intermediate amount of impinging imaging radiation.

In some embodiments, the combination of a radiolucent outer layer with localized regions of radiopaque marking allows clear identification of a screw position, with the radiopaque markers themselves being placed away from (and/or so as to avoid shadowing and/or otherwise affecting the imaging of) tissue regions where clear imaging is most crucial. Optionally, radiopaque markers are generally confined to regions of the screw that stay outside the bone, and/or away from the screw tip (distal end). Optionally, radiopaque marking is sized and/or composed to allow identification of a marker at a first wavelength (for example, a relatively soft X-ray wavelength such as 40 KeV), while being relatively transparent at a second wavelength (for example, a relatively hard X-ray wavelength such as 100 KeV). In some embodiments, markers are placed relative to one another, within a screw, or among a plurality of implant components, so as to reduce and/or control artifacts due to combined effects of radiopaque material in different places; for example, streak and/or darkening artifacts. For example, alignments that could cause artifacts to pass through an anatomical region of particular interest are avoided by providing screws that selectively leave out and/or displace radiopaque markers. Additionally or alternatively, alignments are selected by the placement of radiopaque markers to direct artifacts to occur within regions of lower diagnostic concern (to within the implant itself, and/or into tissues away from regions of high concern), and optionally to align artifacts to overlap with each other so that the total image region affected is reduced.

In some embodiments, radiopaque material such as gold, platinum, rhenium, tungsten, tantalum, or another radiopaque material is attached to all or a part of the inner surface of a composite bone screw's outer layer, and/or distributed throughout the composite material body of the screw. The radiopaque material is provided, for example, as a powder, grains, particles, foil, or in another form. Optionally, the radiopaque material is uniformly distributed over the inner surface of the outer layer (for example, as a coating and/or foil on one side of an outer foil). Potentially, where a preferred thickness of an outer metallic coating is too thin to give a preferred characteristic of radiopacity (a thin foil may be preferred, for example, for its mechanical shaping characteristics), it is an advantage to add a material with a higher linear attenuation coefficient that allows thickness to remain low while increasing radiopacity.

Optionally, the radiopaque part is localized to one or more of the major structural regions of the screw (shaft, tip, and/or head, for example). Optionally, the radiopaque part is sparsely distributed as distinct concentrations of material in a region of the screw, covering, for example, about 1%, 5%, 10%, or another greater, lesser, or intermediate fraction of the surface in the region. Optionally, the radiopaque material is distributed in a pattern which identifies a structural feature of the bone screw and/or a limit of its extent. For example, the radiopacity is positioned to outline the screw shaft or a portion thereof, to identify a limit of the screw tip or head, and/or to identify an axial and/or rotational orientation of the screw.

Potentially, one or more of the above placements and/or constructions of radiopaque markers allows identification of screw position compatible with imaging of hard and/or soft tissue to within 3 mm, 2 mm, 1 mm or intermediate or even smaller distances from the construct, optionally to within a diagnostic quality.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1B:
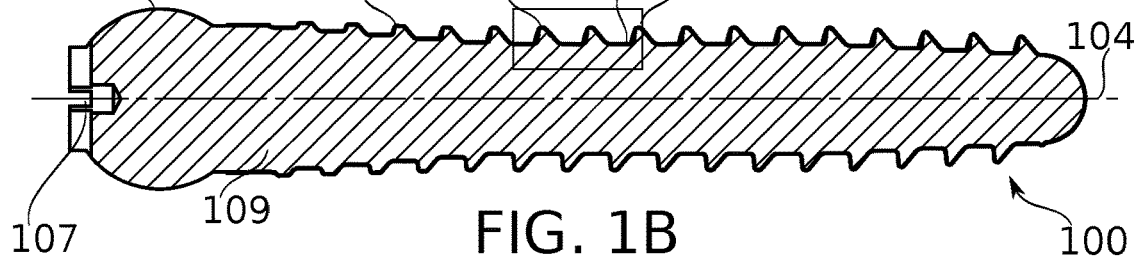

Reference is now made to FIGS. 1A-1B, which schematically illustrate in profile (FIG. 1A) and in cross-section (FIG. 1B) a composite construction bone screw 100 having a metallic outer layer 110, according to some exemplary embodiments of the invention. FIG. 1B represents a cross-section along line A-A.

In some embodiments, a bone screw 100 comprises a head 105 and a shaft 103 extending along a central longitudinal axis 104. Head 105 is optionally formed with proximal region 107 shaped to receive torquing force for rotating the screw into a receiving bone plate and/or bone.

In some embodiments, the screw comprises a diameter (e.g., a diameter of the shank with the thread or a diameter of the shank without the thread) within a range of, for example, between 4.5-8.0 mm; or another longer or shorter diameter.

Optionally the screw has a larger diameter nearer to head 105 (for example, 6.0 mm, 6.5 mm, 7.0 m, 8.0 mm, 8.5 mm, or another larger, smaller, or intermediate diameter), that decreases towards the distal end. Optionally, the screw has a longitudinal length within a range of, for example, between 30-65 mm, or another longer or shorter longitudinal length. The screw pitch optionally is in a range, for example, of between 0.8 mm and 6 mm, and/or within another range having the same, longer, shorter, and/or intermediate bounds.

In some embodiments, bone screw 100 comprises an internal body 109 of composite material construction (for example, CFR-PEEK), and an outer layer 110 of metallic construction (for example, a foil, coating, tube, and/or shell of titanium, titanium alloy, and/or another metal between 1-200 μm thick (optionally anodized); or another layer construction, for example as described elsewhere herein). In some embodiments, the internal body 109 is cannulated.

In some embodiments, a region comprising portion 150 along the shaft 103 of the screw 100 comprises a plurality of screw thread windings, including raised thread portions 101, and the valleys of inter-thread portions 102.

Figure 1C:
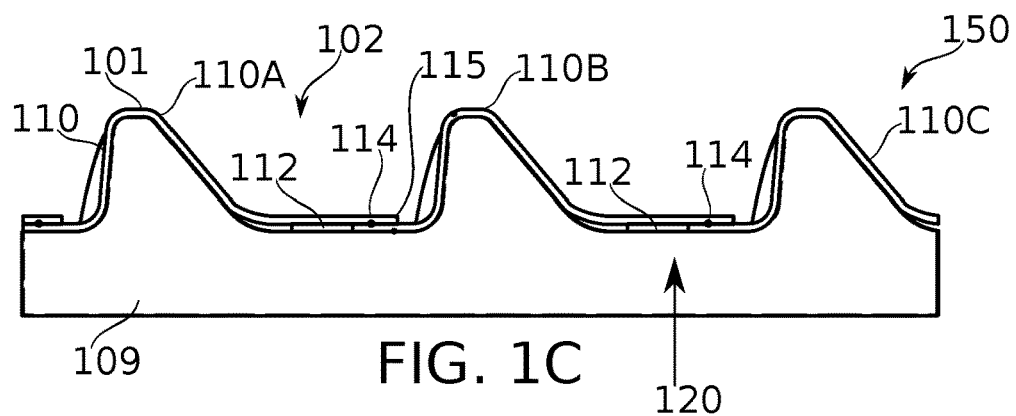
FIG. 1C schematically illustrates a portion of a cross-section of bone screw, including a metallic layer comprising windings, according to some exemplary embodiments of the invention.
Figure 1D:
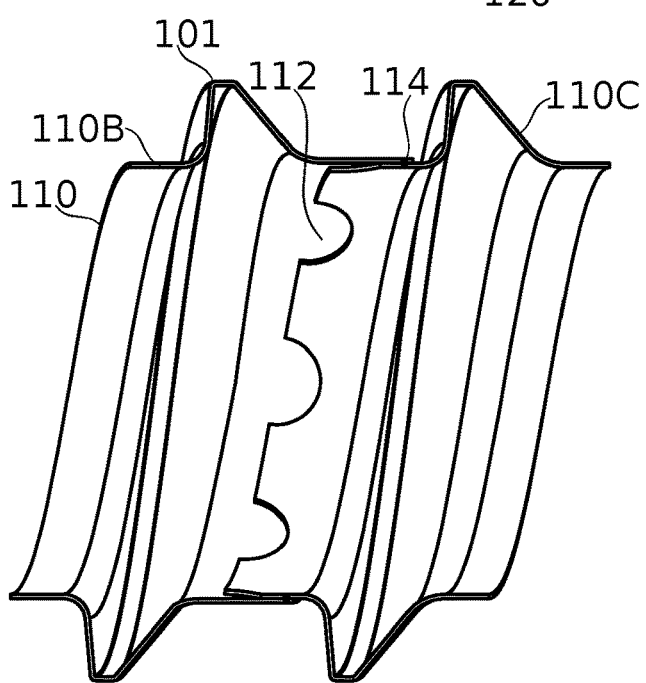
FIG. 1D schematically illustrates an interior view of metallic layer windings of FIG. 1C, according to some exemplary embodiments of the invention.

Reference is now made to FIG. 1C, which schematically illustrates a portion 150 of a cross-section of bone screw 100, including a metallic layer 110 comprising windings 110A, 110B, and 110C, according to some exemplary embodiments of the invention. Reference is also made to FIG. 1D, which schematically illustrates an interior view (from direction 120 of FIG. 1C) of metallic layer windings 110B, 110C, according to some exemplary embodiments of the invention. Further reference is made to FIG. 1F, which schematically illustrates an interior view (also from direction 120 of FIG. 1C) of alternative anchoring structures for metallic layer windings 110B, 110C, according to some exemplary embodiments of the invention. In FIGS. 1D and 1F, the view of composite screw body 109 is suppressed to allow viewing the inner structure of layer 110.

In some embodiments, a metallic layer 110 of bone screw 100 comprises a plurality of windings 110A, 110B, 110C that at least partially encase the shaft 103 of the bone screw 100.

In some embodiments, an edge of metallic layer 110 is shaped with protrusions and/or recesses 112. A scalloped sequence of semi-circular cutouts is shown in FIG. 1D. Additionally or alternatively, the edge shape comprises a repeating pattern, for example, combed, crenellated, toothed, dovetailed, undulated, wave, and/or another regular or irregular pattern. In some embodiments, the edge shape is irregular and non-repeating. In some embodiments, a portion of the outer layer material is perforated (for example, a portion near but not breaking an edge, such as aperture 144 in FIG. 1F), creating a plurality of holes through the material.

Optionally, during manufacture, the screw is subjected to conditions of temperature and pressure (for example, compression molding at 400° C., or another higher, lower, or intermediate temperature), such that material of screw body 109 enters into open volume (for example, cut away regions 112) of metallic layer 110. In some cannulated embodiments, the cannula is introduced during layup of the body and preserved during molding by use of a removable insert. In some embodiments, the cannula is bored into the screw body 109 after molding. Optionally, the cannula diameter is sized to accommodate a K-wire; for example, a K-wire with a diameter in a range between about 0.7 mm-1.6 mm, or a larger or smaller K-wire. The diameter of the cannula is, for example, about 0.8 mm, 1.0 mm, 1.2 mm, 1.4 mm, 1.6 mm, 1.8 mm, or another larger, smaller, or intermediate diameter.

In some embodiments, one of an adjacent pair of windings (for example, winding 110A) partially overlaps the other (for example, winding 110B). In some embodiments, the overlap covers the open areas of metallic layer 110, so that the surface of the screw shaft 103 still receives the protection of a metal covering at those areas.

In some embodiments, the region of overlap comprises one or more weld regions 114, for example, regions where two layers are laser welded together (continuously or at intervals, for example). Potentially, this allows shifting of shear force experienced by the outer layer to the region of body/metal layer anchoring at 112, to resist detachment.

In some embodiments, a single strip (for example, a titanium tape) is wound over itself along the length of the screw threads. Optionally a plurality of strips is wound along the screw threads. A single, self-overlapping strip winding is a potential advantage for reducing a number of exposed edges.

Optionally, the pitch of the winding is kept to the same pitch as the screw threads. This is a potential advantage for protecting a free edge 115 of the overlap region, by keeping it within a constant position within the repeating thread pattern, and/or by keeping it substantially parallel to the direction of greatest shear force to resist peeling. Optionally, the free edge 115 is placed at a portion of the thread valley 102 (for example in the "shadow" of the protruding thread 101) where it is relatively protected from direct shearing contact.

In some embodiments, the strip is about the width of a single thread spacing (the thread pitch being, for example, about 0.8 mm, 1.0 mm, 1.3 mm, 1.5 mm, 1.8 mm, 2.0 mm, 2.2 mm, or another longer shorter or intermediate pitch), plus additional width for overlap. Optionally, the additional width for overlap is about 20% of a thread spacing, 30%, 40%, or another greater, smaller, or intermediate fraction of a thread spacing. Optionally, the screw has more than one thread.

In some embodiments, the strip spans two, three, or more windings. This optionally results in multiple layers at some or all points along the shaft. Intermediate layer regions are optionally welded to the layer below, and/or provided with openings that align with openings of the layer beneath into which screw body material penetrates for fixation.

In some embodiments, a winding pitch of a layer is different than (longer, shorter, and/or in an opposite winding direction) the thread pitch. A longer pitch reduces the length of the exposed edge region (by requiring fewer windings), that provides a potential advantage by exposing a shorted edge length requiring attachment. In the limit of this, an outer layer strip overlaps itself (or another strip) with an edge extending along longitudinal axis 104, producing a shell-like configuration. Optionally, the shell is a whole shell, split along a single seam.

Optionally, a plurality of shell portions mate to enclose the screw body along two or more seams. Optionally, anchoring to reduce a risk of peeling by a thread-crossing edge experiencing shear forces during insertion or removal is provided by thin strip or wire wound at the thread pitch.

In some embodiments, the metallic outer layer comprises at least one tubular metallic ply, compressed one on top an underlying anchor ply. Optionally, an inner tubular ply is perforated to allow penetration by the matrix of the screw body material upon compression, and a solid outer tubular ply is secured to the inner ply by welding (for example laser welding). In some embodiments, an outer ply is coated onto an inner ply and/or the composite material of the screw body by another means (for example, sputter coating, electroplating, or another method where a sheet of metal forms on the device itself), with the anchored ply serving as a shear-resistant base. Alternatively, the inner ply comprises a shell or a wound strip. Optionally, the inner ply only partially covers the body (for example, covers no more than 5%, 25%, 40%, 60%, 80%, or another greater, lesser, or intermediate fraction of the body, and/or of a threaded region of the body), serving primarily as an anchor for a fuller outer covering ply.

Figure 2A:
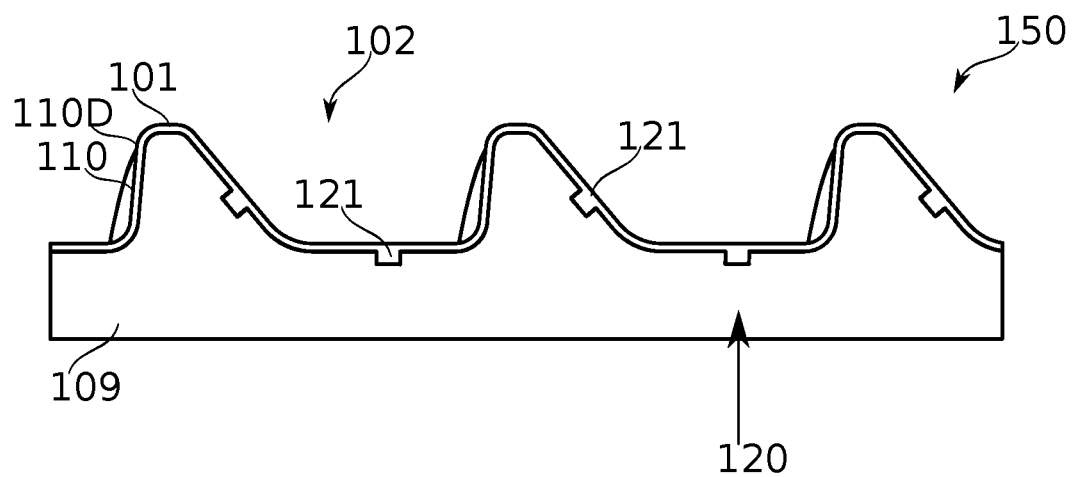
FIG. 2A schematically illustrates an alternative embodiment of a metallic layer at a portion of a cross-section of a bone screw, the layer comprising a plurality of inwardly protruding anchors, according to some exemplary embodiments of the invention.

Reference is now made to FIG. 2A, which schematically illustrates an alternative embodiment of metallic layer 110 (metallic layer 110D) at portion 150 of a cross-section of a bone screw 100, layer 110D comprising a plurality of inwardly protruding anchors 121, according to some exemplary embodiments of the invention. Reference is also made to FIGS. 2C-2D, which schematically illustrate alternative structures of anchor 121 on the interior of a metallic layer 110 according to some exemplary embodiments of the invention.

In some embodiments, an outer layer 110 comprises a tubular member 110D to which is attached a plurality of projecting anchors 121 on its inner side. Upon compression molding, anchors 121 press into the material of body 109, helping to increase the resistance of layer 110 to movement and/or rupture under the shearing forces of insertion and/or removal.

In some embodiments, anchors 121 comprise metal of the same composition as layer 110, for example titanium or titanium alloy. Additionally or alternatively, anchors 121 comprise another material that can be welded to the metal of layer 110, and/or encapsulated to allow this welding, for example encapsulated by titanium or titanium alloy. In some embodiments, the non-titanium material comprises a radiopaque substance that serves as a marker, for example, gold, platinum, rhenium, tungsten, tantalum, or another radiopaque material. It is a potential advantage to provide markers at places along the screw 100 and near the screw surface, to allow the screw to be delineated under radiographic imaging. In some embodiments, the markers are sufficiently radiopaque to be visible in an image, but not large enough and/or opaque enough to substantially prevent the visualization of tissues alongside the screw; or to prevent visualization within, for example, 1 mm, 2 mm, 3 mm, or another greater, smaller, and/or intermediate distance of the markers. Optionally, visualization is not prevented when any artifacts that do occur are smaller in magnitude than, for example, 5% of the baseline image intensity values (values in the absence of artifact), 10%, 20%, 40%, or another greater, smaller, and/or intermediate artifact size.

In some embodiments, anchors 121 comprise grains, wires, blocks, billets, disks (such as disk 148), and/or another shape. In some embodiments, anchors 121 themselves comprise one or more connected regions 147, and at least one additional protrusion (for example, a barb, and/or unconnected anchor leaf 149) that act as a hook to resist pulling out of the composite material matrix.

Discrete anchors are optionally provided at fixed intervals in relation to the thread pitch of the screw, and/or at irregular or random intervals. Percent coverage of the interior of layer 110 with anchor structures is for example, about 1%, 5%, 10%, 20%, or another greater or lesser fraction.

The thickness of an anchor (depth of penetration into the screw body 109) is, for example, in the range of about 50-100 μm, or another greater or lesser thickness.

Optionally, the anchor increases the thickness of the metallic outer layer and/or a ply of the metallic outer layer by at least 10%, 25%, 50%, 75%, 100%, or by at least another greater, lesser, and/or intermediate fraction. Other dimensions of the anchor can be any size, from a small fraction of a pitch width (for example, 100 μm or less) to a continuous length of wire extending, for example, along substantially the whole length of a wound metallic strip, or wound within and along substantially the whole length of a metallic tube.

A wire anchor is optionally provided as an interior winding of the metallic layer in some fixed relation to the thread pitch of the screw (for example, the same as the screw pitch, or a multiple of fraction thereof). Where layer 110 comprises a wound metallic strip, anchors 121 optionally comprise a plurality of wires extending across all or a portion of the width of the strip at intervals.

In some embodiments, anchors 121 comprise a mesh, or an array of mesh patches.

In FIG. 2A, layer 110D comprises a single tubular metallic ply; however it is to be understood that the inwardly protruding anchors 121 described in relation to layer 110D are optionally provided to a ply of wound metallic strip or shell, for example as described in relation to FIGS. 1C-1D. In some embodiments, a first anchoring layer comprises a wire wound, for example, between the threads 101 of the screw (optionally, a wire spaced at intervals with anchoring structures 121), to which an outer metallic ply is attached, for example, by welding.

Figure 1E:
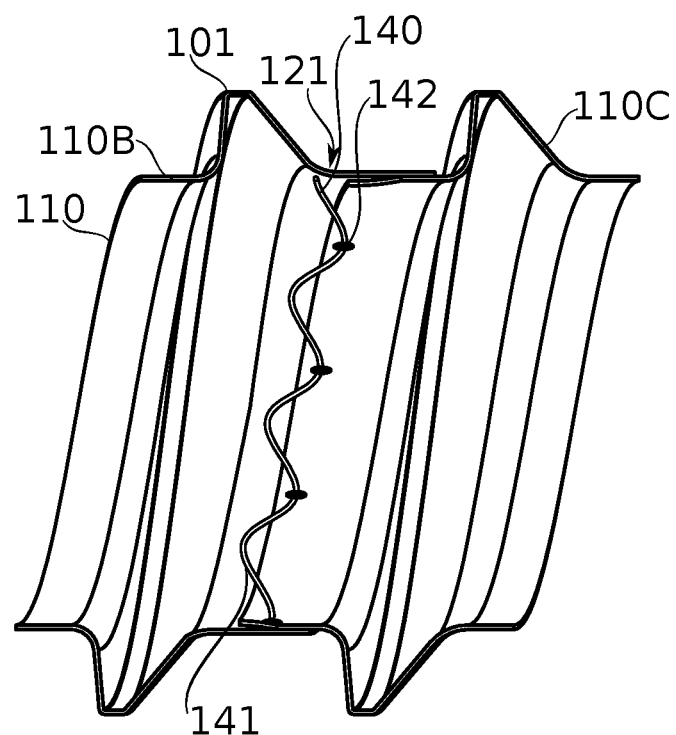
FIGS. 1E-1F schematically illustrate interior views of alternative anchoring structures for metallic layer windings, according to some exemplary embodiments of the invention.
Figure 1F:
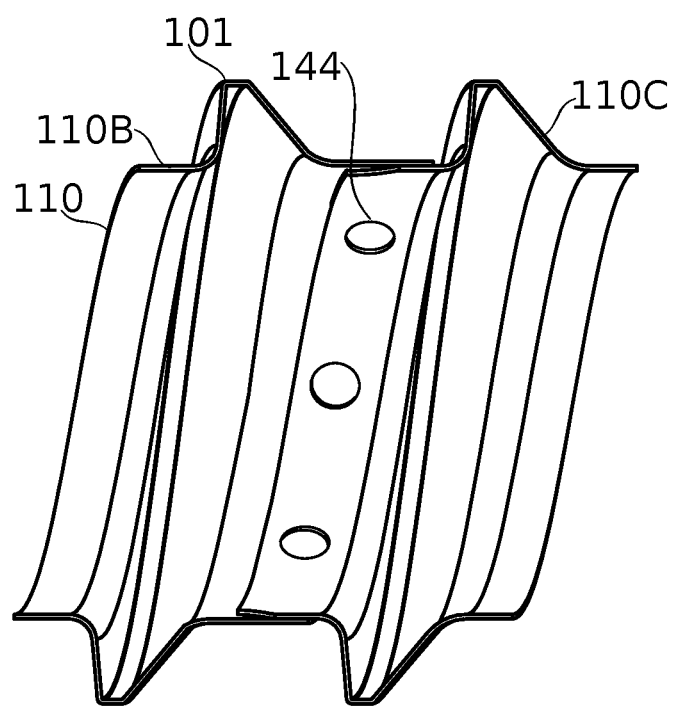

Reference is now made to FIG. 1E, which schematically illustrates an interior view (from direction 121 of FIG. 1C) for metallic layer windings 110B, 110C, according to some exemplary embodiments of the invention. In FIG. 1E, the view of composite screw body 109 is suppressed to allow viewing the inner structure of layer 110.

In some embodiments, anchor 121 comprises loops 141 of wire 140 and/or mesh, attached at intervals (for example, at weld points 142) along the inside of layer 110. Potentially, loops 141 embed into the matrix material of the screw body 109, such that disruption of metallic outer layer attachment requires breaking the loop and/or the matrix in which it is embedded. Optionally, anchoring loops 141 are provided to the inside of a tube and/or shell structure.

Figure 2B:
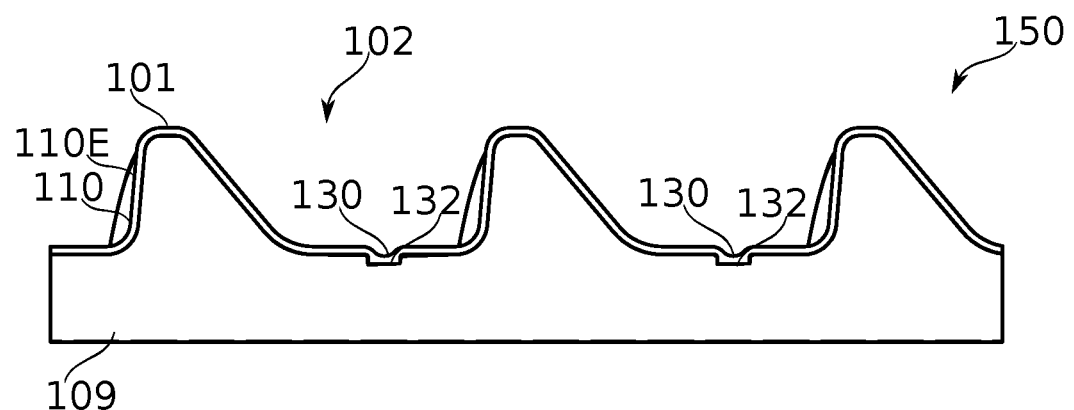
FIG. 2B schematically illustrates an alternative embodiment of a metallic layer at a portion of a cross-section of a bone screw, the layer comprising a plurality of indentations displacing portions of composite screw body, according to some exemplary embodiments of the invention.
Figure 2C:
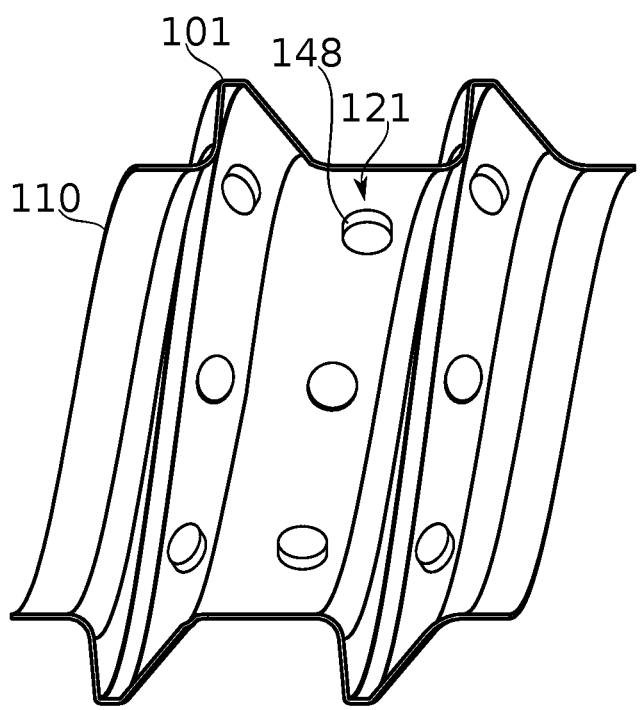
FIGS. 2C-2D schematically illustrate interior views of alternative anchoring structures for anchoring a metallic layer, according to some exemplary embodiments of the invention.
Figure 2D:
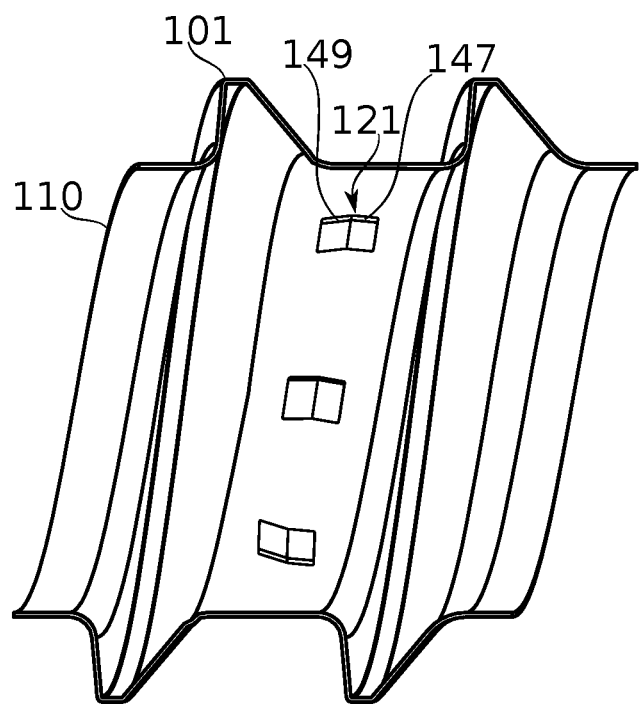

Reference is now made to FIG. 2B, which schematically illustrates an alternative embodiment of metallic layer 110 (metallic layer 110E) at portion 150 of a cross-section of a bone screw 100, layer 110E comprising a plurality of indentations 130 displacing portions 132 of composite screw body 109, according to some exemplary embodiments of the invention.

In some embodiments, an outer layer 110 comprises a thin metallic tube 110E which, in addition to being compressed to conform with the threads 101 of body 109, is also stamped, mold compressed, or otherwise deformed to provide indentations 130 that intrude at intervals into the matrix material of body 109, so that an interlocking system of layer indentations 130 and receiving divots 132 in the body is formed. For example, a mold is formed with bumps in suitable locations (optionally, between thread windings) to press indentations into the metallic layer. Optionally, the indentations are made at intervals along the threaded shaft 103 of the bone screw 100, for example, 1, 2, 3, 4, 5, 6, or more indentations per thread step. Optionally, the indentations are made within the inter-thread spaces 102 along the shaft 103. This is a potential advantage to avoid disturbing the shape of the threads 101.

In some embodiments, a metallic strip or shell portion instead of a tube is indented. Optionally a second ply of the metallic outer layer is welded or otherwise attached to an inner layer. This potentially fairs (smooths out) the screw surface, while still taking advantage of shear-resistance created by the geometrical interlocking of the inner layer.

Figure 3:
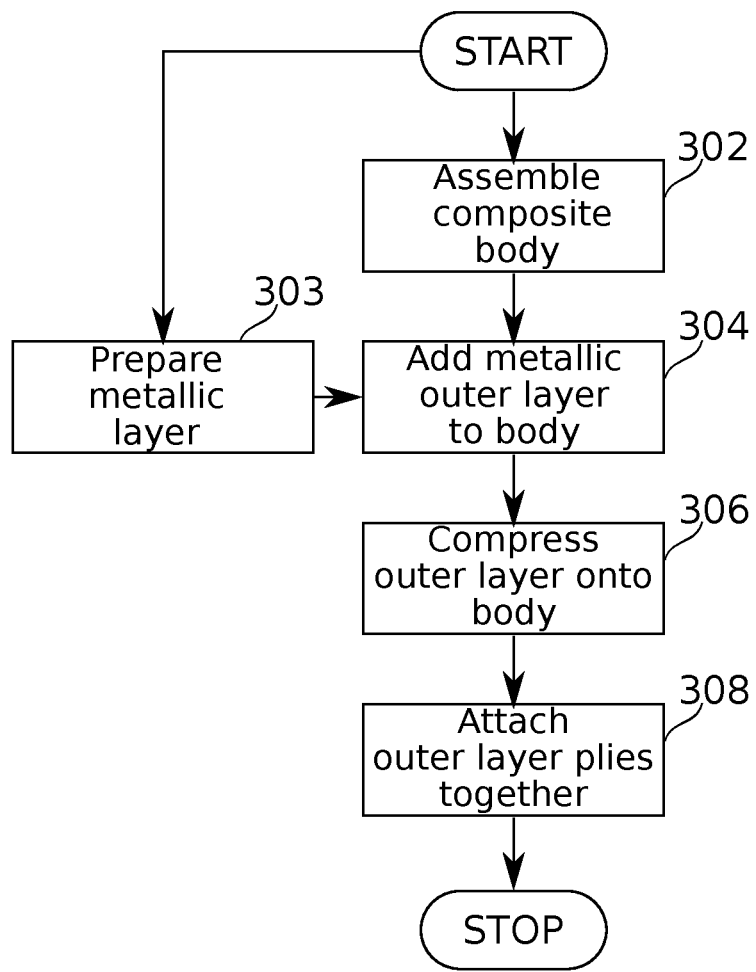
FIG. 3 is a schematic flowchart of the assembling of a composite material screw geometrically interlocked to a metallic outer layer, according to some exemplary embodiments of the invention.

Reference is now made to FIG. 3, which is a schematic flowchart of the assembling of a composite material screw geometrically interlocked to a metallic outer layer, according to some exemplary embodiments of the invention.

At block 302, in some embodiments, a composite material constructed screw body is assembled. The screw body comprises, for example, one or more layers of CFR-PEEK tape, optionally overlaid in different directions. This form of construction is potentially as strong as metal body construction, while reducing stress shielding of bone to which the screw is attached. Moreover, the composite material is more radiolucent than an all-metal implant, with potential advantages for reducing image artifacts associated with implant monitoring or imaging of tissues around the implant.

However, it is a potential advantage to provide the surface qualities of a metal to the screw; for example, properties of toughness, biocompatibility, and/or even appearance.

At block 303, in some embodiments, a metallic layer is prepared for assembly to the body of the screw. Optionally, the layer is initially in the form of a tube, sheet, or strip (tape). In some embodiments, preparation comprises cutting, perforating, and/or scoring the layer, for example cutting shapes for interlocking into the edge, punching holes through the material, or cutting irregularities such as grooves into the surface of the layer.

Additionally or alternatively, preparation comprises attaching anchors of any suitable shape to an inner surface of the layer. Anchors are optionally attached separately, as loops between attachment points, as a granulated coating, or in any other suitable manner. In some embodiments, where an embossed attachment is to be formed, the layer is pre-embossed; however, this step is optionally performed later.

At block 304, in some embodiments, the metallic outer layer is added to the composite material body—for example, wrapped around it (as for a strip), slipped over it (as for a tube), closed around it (as for a shell), or otherwise put into position.

At block 306, in some embodiments, the composite material body is compressed onto the metallic outer layer. Optionally, this is performed with a combination of heat (for example enough heat to melt the composite matrix) and pressure. The temperature is, for example, about 400° C., or another temperature.

In some embodiments, the hot compression causes composite material matrix to flow into prepared spaces of the metallic outer layer, and/or be forced away by prepared protrusions of the metallic outer layer. In some embodiments, the mold itself contains shapes that press anchoring shapes (such as indentations) into the outer layer and/or the underlying matrix material.

In some embodiments, blocks 304 and 306 are repeated; for example, if a second or subsequent metallic ply is to be provided atop an anchoring ply after a first molding operation.

At block 308, post-compression operations occur. In some embodiments, overlapping plies (of one strip, or of a plurality of strips or other separately applied plies such as a tube or shell piece) are welded together. In some embodiments, stamping of anchoring indentations occurs after compression of the outer layer to the screw body. Optionally, stamping is performed at a high temperature that softens the matrix, for example, before the part fully cools after compression, or with at least partial re-heating.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of manufacturing a screw comprising:
   providing a screw body formed from a composite material comprising a fiber-reinforced polymer matrix;
   surfacing the screw body with a metallic layer of overlapping metallic plies, said metallic layer covering at least screw threads of the screw;
   attaching the metallic layer onto the screw body by compression molding.
2. The method according to claim 1,
   wherein said metallic layer resists a shearing force applied to the metallic layer when the screw is rotated within the bone.
3. The method according to claim 1, wherein a free edge of an overlap region of the metallic plies is located at a portion of a thread valley between adjacent said screw threads.
4. The method according to claim 1, wherein the metallic layer comprises at least one from among the group comprising titanium and a titanium alloy.
5. The method according to claim 4, wherein the titanium or titanium alloy is anodized.
6. The method according to claim 1, wherein said metallic layer comprises Ti6Al4V.
7. The method according to claim 1, wherein the metallic layer has a thickness in the range of from 0.1-0.02 mm.
8. The method according to claim 1, further including one of laser welding, sputter coating, electroplating, and another method where a sheet of metal forms on the device itself to attach at least some consecutive said overlapping metallic plies to each other or to said screw body in a region of overlap.
9. The method according to claim 1, wherein the screw is cannulated.
10. The method according to claim 1, wherein said surfacing the screw body with the metallic layer of overlapping metallic plies includes winding a strip around the body.
11. The method according to claim 10, wherein said surfacing includes overlying and welding a first portion of the strip to a second portion of the strip.
12. The method of claim 11, wherein a free edge of the first portion of the strip lies in a recess between two turns of the screw threads.
13. The method according to claim 1, wherein at least one of the plurality of metallic plies comprises a tube and wherein said surfacing includes compressing said tube onto the body.
14. The method according to claim 13, wherein said surfacing includes welding said tube to another ply of said metallic layer.
15. The method according to claim 1, wherein said surfacing includes forming a plurality of anchor structures out of material of the plurality of overlapping metallic plies to engage with the composite material.
16. The method according to claim 15, wherein the anchor structures have a thickness dimension at least 50% of the thickness of said metallic plies.
17. The method according to claim 15, wherein said forming the plurality of the anchor structures include indentation of an outer surface of the plurality of metallic plies.
18. The method according to claim 17, wherein the indentation is within a recessed region between two turns of the screw threads.
19. The method according to claim 17, wherein the indentation protrudes by at least 50% of the thickness of the plurality of metallic plies into the composite material, relative to a non-indented surrounding inner surface of the metallic layer.
20. The method according to claim 15, wherein said surfacing includes forming the anchor structures in a repeating pattern along the metallic layer.
21. The method according to claim 1, wherein said surfacing includes forming a plurality of anchor structures in the plurality of metallic plies as openings filled with said composite material.
22. The method according to claim 21, wherein the openings are formed as one of:
   convolutions of an edge of at least one metallic ply; and
   apertures in at least one metallic ply.

23. The method according to claim 1, wherein said metallic layer further covers a non-threaded region of said screw.

24. The method according to claim 1, wherein said attaching includes winding the metallic plies around the screw body.

25. The method according to claim 1, further including, before said attaching:
- shaping the metallic layer to include a plurality of anchoring structures;
- wherein, when the metallic layer is attached to the screw body, the plurality of anchoring structures interpenetrate with the composite material of the bone screw body underneath recesses defined between adjacent thread windings of the bone screw.

* * * * *